(12) United States Patent
Stamnes et al.

(10) Patent No.: US 9,974,475 B2
(45) Date of Patent: May 22, 2018

(54) OPTICAL TRANSFER DIAGNOSIS (OTD) METHOD FOR DISCRIMINATING BETWEEN MALIGNANT AND BENIGN TISSUE LESIONS

(71) Applicant: Balter Inc., Maplewood, NJ (US)

(72) Inventors: Jakob J. Stamnes, Oslo (NO); Boerge Hamre, Sandsli (NO); Gennady Ryzhikov, Loddefjord (NO); Lu Zhao, Bergen (NO); Marina Buryulina, Loddefjord (NO); Knut Stamnes, Maplewood, NJ (US)

(73) Assignee: Balter, Inc., Maplewood, NJ (US)

( * ) Notice: Subject to any disclaimer, the term of this patent is extended or adjusted under 35 U.S.C. 154(b) by 0 days. days.

(21) Appl. No.: 14/755,765

(22) Filed: Jun. 30, 2015

(65) Prior Publication Data

US 2015/0297130 A1    Oct. 22, 2015

Related U.S. Application Data

(63) Continuation-in-part of application No. 12/933,037, filed as application No. PCT/US2009/037511 on
(Continued)

(51) Int. Cl.
*A61B 5/00* (2006.01)
*A61B 5/107* (2006.01)

(52) U.S. Cl.
CPC ............ *A61B 5/444* (2013.01); *A61B 5/0075* (2013.01); *A61B 5/0077* (2013.01); *A61B 5/1079* (2013.01); *A61B 5/7264* (2013.01)

(58) Field of Classification Search
None
See application file for complete search history.

(56) References Cited

U.S. PATENT DOCUMENTS

| 5,813,988 A | 9/1998 | Alfano et al. |
| 6,081,612 A | 6/2000 | Gutkowicz-Krusin et al. |

(Continued)

FOREIGN PATENT DOCUMENTS

| JP | 2003-149136 A | 5/2003 |
| JP | 2005-192944 A | 7/2005 |

(Continued)

OTHER PUBLICATIONS

Chun et al. ("A nonlinear estimation algorithm, and its optical implementation for the target tracking in clutter environment", SPIE vol. 3961;2000).

(Continued)

*Primary Examiner* — G. Steven Vanni
(74) *Attorney, Agent, or Firm* — Brown Rudnick LLP; Mark S. Leonardo

(57) ABSTRACT

An embodiment of the present invention includes a method for discriminating between benign and malignant tissue lesions. The method includes the steps of using a plurality of maps of physiology and morphology parameters generated from reflectance measurements and morphology parameters generated from reflectance measurements. The method also includes calculating entropies and cross entropies of the plurality of maps, and calculating a plurality of morphology parameters. Further, the method includes assigning a weight to each entropy and a weight to a logarithm of each entropy, a weight to each cross entropy and a weight to a logarithm of each cross entropy, and a weight to each morphology parameter and a weight to a logarithm of each morphology parameter. The method further includes computing a diagnostic index, defining a cost function, defining a proper threshold value for a diagnostic index and solving an optimization problem to determine a set of weights from the assigned weights to maximize specificity for 100% sensitivity. Further, the method uses calculations, the cost function and the diagnostic index to determine whether the tissue lesion is benign or malignant.

13 Claims, 8 Drawing Sheets

Related U.S. Application Data

Mar. 18, 2009, now Pat. No. 9,823,189, and a continuation-in-part of application No. 12/864,388, filed as application No. PCT/US2009/031969 on Jan. 26, 2009, now abandoned.

(60) Provisional application No. 61/037,503, filed on Mar. 18, 2008, provisional application No. 61/023,242, filed on Jan. 24, 2008.

(56) References Cited

U.S. PATENT DOCUMENTS

| | | | |
|---|---|---|---|
| 6,208,749 | B1 | 3/2001 | Gutkowicz-Krusin et al. |
| 6,307,957 | B1 | 10/2001 | Gutkowicz-Krusin et al. |
| 6,324,417 | B1 | 11/2001 | Cotton |
| 2001/0032053 | A1 | 10/2001 | Hielscher et al. |
| 2004/0030255 | A1 | 2/2004 | Alfano et al. |
| 2004/0092824 | A1 | 5/2004 | Stamnes et al. |
| 2005/0251049 | A1 | 11/2005 | Cane et al. |
| 2007/0016078 | A1 | 1/2007 | Hoyt et al. |
| 2007/0269804 | A1 | 11/2007 | Liew et al. |
| 2009/0134331 | A1 | 5/2009 | Miyamae et al. |

FOREIGN PATENT DOCUMENTS

| | | | |
|---|---|---|---|
| JP | 2007-190364 A | | 8/2007 |
| WO | 00/37924 A1 | | 6/2000 |
| WO | 02/27660 A2 | | 4/2002 |
| WO | 2006/076810 A1 | | 7/2006 |
| WO | 2007026884 A1 | | 3/2007 |
| WO | 2009/094623 A2 | | 7/2009 |
| WO | 2009/117485 A2 | | 9/2009 |

OTHER PUBLICATIONS

Claridge E et al: "Shape Analysis for Classification of Malignant Melanoma", Journal of Biomedical Engineering, Butterworth, Guildford, GB, vol. 14, No. 3, May 1992 (May 1992), pp. 229-234.

Extended European Search Report dated Nov. 30, 2015 for European Patent Application No. 15186132.5 (9 Pages).

Ganster H et al: "Automated Melanoma Recognition", IEEE Transactions on Medical Imaging, IEEE Service Center, Piscataway, NJ, US, vol. 20, No. 3, Mar. 2001 (Mar. 2001), pp. 233-239.

Hannen, Egied J. M. et al. An Image Analysis Study on Nuclear Morphology in Metastasized and Non-metastasized Squamous Cell Carcinomas of the Tongue. Journal of Pathology. 1998, vol. 185, pp. 175-183 See p. 176, col. 1, Line 37—p. 177, col. 2, Line 57.

International Search Report and Written Opinion for PCT/US2009/031969 dated Sep. 1, 2009.

International Search Report and Written Opinion for PCT/US2009/037511 dated Dec. 2, 2009.

Iyatomi et al., 2006, Quanitifcation of clinical items of dermoscopy for computer-based melanoma diagnosis, Proceedings of the Fuzzy System Symposium (CD-ROM) 22:387-392.

Jacques et al. ("Internal absorption coefficient and threshold for pulsed laser disruption of melanosomes isolated from retinal pigment epithelium", SPIE vol. 2681, 1996).

Machine Translated Notice of Reasons for Rejection with a Patent Application No. 2014-049729 dated Feb. 24, 2015 (3 pages).

Notice of Reasons for Rejection in related Japanese application JP2011500922, dated Nov. 19, 2013 [Translation].

Rallan, Deepak et. al. Quantitative Discrimination of Pigmented Lesions Using Three-Dimensional High-Resolution Ultrasound Reflex Transmission Imaging. Journal of Investigative Dermatology. Oct. 2006, vol. 127, pp. 189-195 See p. 190, col. 2, Line 1—p. 191, col. 2, Line 16.

Rolston et al. "A Well Collimated Quasi-Continuous Atom Laser". Mar. 4, 2000. http://web.archive.org/web/20000304120946/http://physics.nist.gov/Divisions/Div842/Gp4/AtomOptics/intro.html.

Sboner A et al: "A Multiple Classifier System for Early Melanoma Diagnosis", Artificial Intelligence in Medicine, vol. 27, No. 1, 2003, pp. 29-44.

Seidenary et al. ("Digital videomicroscopy improves diagnostic accuracy for melanoma"; department of Dermatology, University of Modena; Apr. 10, 1998).

Siegel, A.M., J.J.A. Marota, and D.A. Boas. "Design and evaluation of a continuous-wave diffuse optical tomography system". 1999. Optics Express. vol. 4, No. 8, pp. 287-298.

OPTICAL TRANSFER DIAGNOSIS (OTD) METHOD FOR DISCRIMINATING BETWEEN MALIGNANT AND BENIGN TISSUE LESIONS

CROSS REFERENCE TO RELATED CASES

This application is a continuation-in-part of U.S. patent application Ser. No. 12/864,388, filed Nov. 15, 2010, which is a National Stage Entry of International Patent Application Serial No. PCT/US09/31969, filed Jan. 26, 2009, which claims priority to U.S. Provisional Application Ser. No. 61/023,242, filed Jan. 24, 2008 and U.S. Provisional Application Ser. No. 61/037,503, filed Mar. 18, 2008, each of which is incorporated herein by reference in their entirety. This application is also a continuation-in-part of U.S. patent application Ser. No. 12/933,037, filed Nov. 15, 2010, which is a National Stage Entry of International Patent Application Serial No. PCT/US2009/037511, filed Mar. 18, 2009, which claims priority to U.S. Provisional Application Ser. No. 61/037,503, filed Mar. 18, 2008, each of which is incorporated herein by reference in their entirety.

FIELD OF THE INVENTION

The present disclosure relates to a method for discriminating between different types of tissue lesions. In particular, the present disclosure is directed to a method for discriminating between malignant and benign tissue lesions.

BACKGROUND

Malignant melanoma is one of the most rapidly increasing cancers in the world. In the United States alone, the estimated incidence for 2008 is 62,480, which leads to an estimated total of 8,420 deaths per year. Successful treatment of melanoma depends on early detection by clinicians with subsequent surgical removal of tumors. Visual detection has its limitations, even when augmented with dermoscopy, especially with less experienced users. In vivo visual analysis of skin lesions typically requires a dermatologist to manually identify characteristics such as asymmetry, irregular borders, color(s), and diameter. The lack of a repeatable, objective, and quantifiable assessment procedure for skin lesions can result in misdiagnoses leaving some cancerous lesions untreated and, on the other end of the spectrum, leading to unnecessary invasive procedures (e.g., biopsies) for further investigation of ultimately benign lesions. Attempts have thus been made to develop automated devices to assist in the screening of pigmented skin lesions for likelihood of melanoma but these devices are expensive and not significantly more accurate than traditional manual review of lesions.

SUMMARY

Systems and methods of the invention relate to discriminating between benign and malignant tissue lesions. The present invention provides tools for skin lesion analysis using an application specific image capturing device used in cooperation with data processing systems that assign numeric values to a number of lesion characteristics indicative of malignancy. Such systems can automate lesion analysis and provide increased accuracy over existing, manual methods, thereby providing advancement in the field of dermatology by decreasing the rate of false positives and unnecessary invasive procedures associated therewith. An embodiment of the present invention includes generating a plurality of spectral reflectance images of a lesion using an optical transfer diagnosis (OTD) device and using data from the skin lesion reflectance images to create maps showing the spatial distribution of a parameter such as hemoglobin oxygenation across the lesion. Entropy measurements of such parameters may be used, along with overall values of various morphology and physiology parameters measured in the lesion, to indicate the likelihood of the lesion being malignant.

A set of reflectance images may be recorded at different wavelengths (e.g., 10 different wavelengths in the range of 365-1000 nm) from multiple angles of illumination (e.g. the positioning of the illumination source relative to the lesion) and detection (i.e. the position of the detector relative to the lesion). The OTD device is configured to generate these images using multiple image sensors and sources of illumination fixed in relation to each other within the device so that the OTD device need only be positioned over the target lesion one time to generate the complete image set. On the basis of established absorption and transmission spectra for known skin chromophores and mathematical modeling of skin reflectance, the images from each set are used to derive maps of the lesions reflecting spatial distribution of the following 7 parameters (i) percentage of hemoglobin; (ii) percentage of hemoglobin oxygenation; (iii) upper epidermal thickness; (iv) lower epidermal thickness; (v) percentage of upper melanosome concentration; (vi) percentage of lower melanosome concentration; and (vii) percentage of keratin concentration. These parameters vary and are different for normal and malignant tissues. In certain embodiments, morphology parameters may be derived from reflectance images of the skin lesion generated by the OTD device.

Steps of the invention include using the maps to calculate entropies and cross entropies for the various parameters that reflect the level of disorder associated with the distribution of that parameter across the lesion. Further, the method may include assigning a weight to each entropy and a weight to the logarithm of each entropy, a weight to each cross entropy and a weight to the logarithm of each cross entropy, and a weight to each morphology parameter and a weight to the logarithm of each morphology parameter. The method further includes computing a diagnostic index, defining a cost function, defining a proper threshold value for a diagnostic index and solving an optimization problem to determine a set of weights from the assigned weights to maximize specificity for 100% sensitivity. Further, the method uses calculations, the cost function and the diagnostic index to determine whether the tissue lesion is benign or malignant.

BRIEF DESCRIPTION OF THE FIGURES

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings as set forth below:

DETAILED DESCRIPTION

The following detailed description refers to the accompanying drawings. The same reference numbers in different drawings may identify the same or similar elements. In addition, the following detailed description does not limit the present disclosure.

The present invention relates to a method for discriminating between different types of tissue lesions. In particular, the present invention is directed to a method for discriminating between malignant and benign tissue lesions. In the present invention, a novel melanoma detection method is taught. The method of the present invention uses maps as well as morphological parameters generated from spectral reflectance images of melanocytic lesions, and which can be extended to discriminate between benign and malignant tissue lesions, in general.

The present invention uses maps of the spatial distribution of various parameters, which are generated by the Optical Transfer Diagnosis (OTD) method, as described in the patent entitled "Method and an Arrangement for the Determination of the Optical Properties of Multi-Layered Tissue", PCT WO 02/069792 A1.

Figure 5:
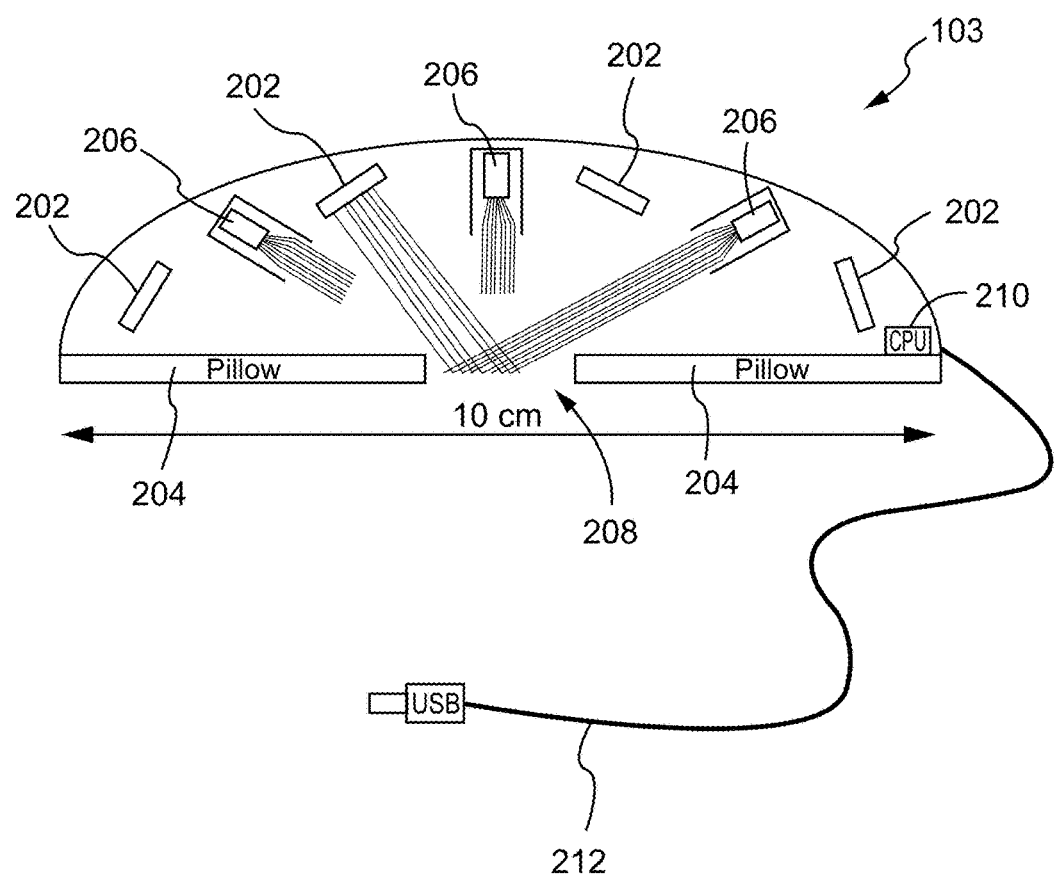
FIG. 5 shows an exemplary OTD device comprising cameras and sources of illumination at varying angles of illumination and detection.

The OTD device used records 30 spectral reflectance images of a lesion under examination. These 30 reflectance images, which constitute one image set, are recorded at 10 different wavelengths (365-1000 nm) from multiple angles of illumination and detection. One version of the OTD device is a spectral reflectance meter consisting of a measurement head with 12 fixed light-emitting diode (LED) lamps and 3 IEEE (Institute of Electrical and Electronics Engineers) 1394 FireWire cameras. Each LED is placed at a different angle relative to the skin to enhance the ability to retrieve information about the depth of the lesion. The polar angles of the LEDs vary between 30 and 45 degrees, and the relative azimuth angles between 34 and 145 degrees. The polar angles of the detectors vary between 0 and 45 degrees, and the relative azimuth angles between 0 and 180 degrees. In the current OTD practice, an alcohol-based gel is used as an interface between the measurement probe and the skin, and a selected area of the skin is illuminated and imaged through a 2.2 cm diameter circular sapphire plate. The imaging time is approximately 5 seconds. FIG. 5 shows an exemplary measurement head 103 with sources of illumination 206, and cameras 202, fixed at angles of illumination and detection relative to a central opening 208 configured to be placed above the skin lesions to be studied. A pillow 204 surrounds the central opening at the point of contact with a patient's skin. The measurement head 103 may include a central processing unit 210 with an electrical connection 212 for a computer such as a Universal Serial Bus (USB) cable.

Figure 3:
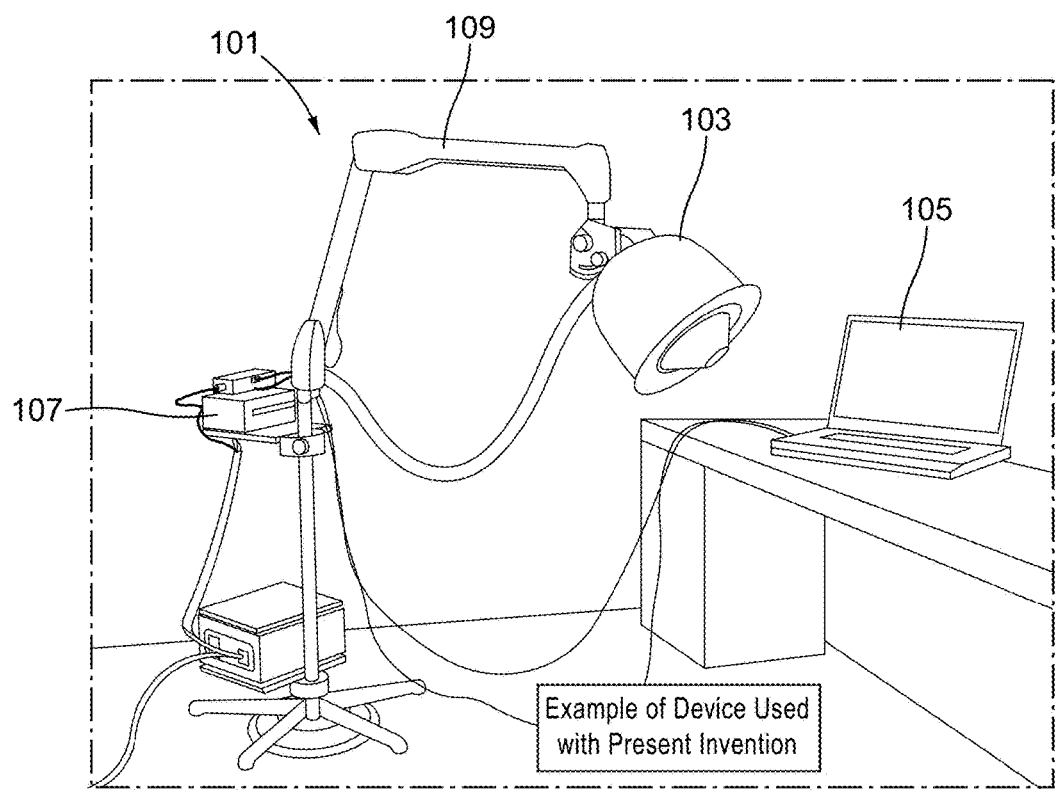
FIG. 3 shows an exemplary system of the invention including an OTD device and a computer.
Figure 4:
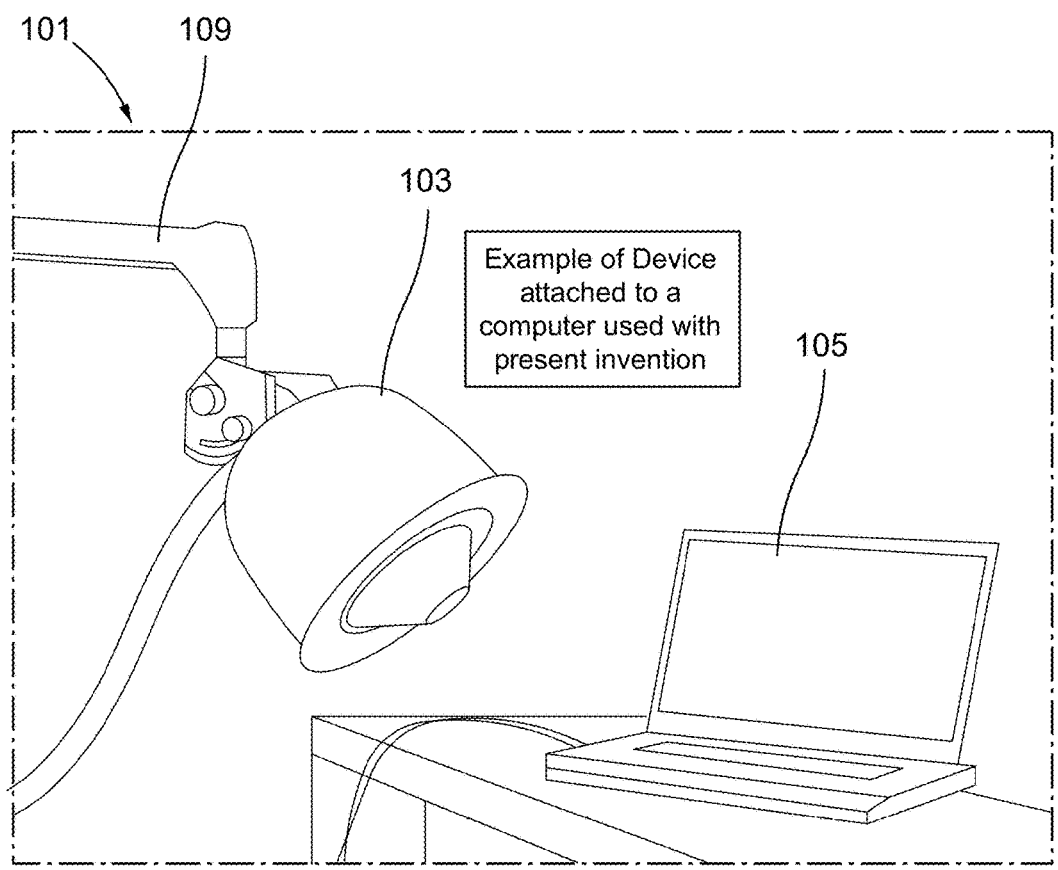
FIG. 4 shows an exemplary system of the invention including an OTD device attached to a computer.

Exemplary systems of the invention, including an OTD device 101 attached to a computer 105 are shown in FIGS. 3-4. FIG. 3 shows an OTD device 101, comprising a measurement head 103, coupled to a support arm 109, in electronic communication with a control unit 107 and a computer 105 for processing and displaying recorded images. FIG. 4 shows another view of an OTD device 101, comprising a measurement head 103, coupled to a support arm 109, in electronic communication with a control unit (not shown) and a computer 105 for processing and displaying recorded images.

Figure 7:
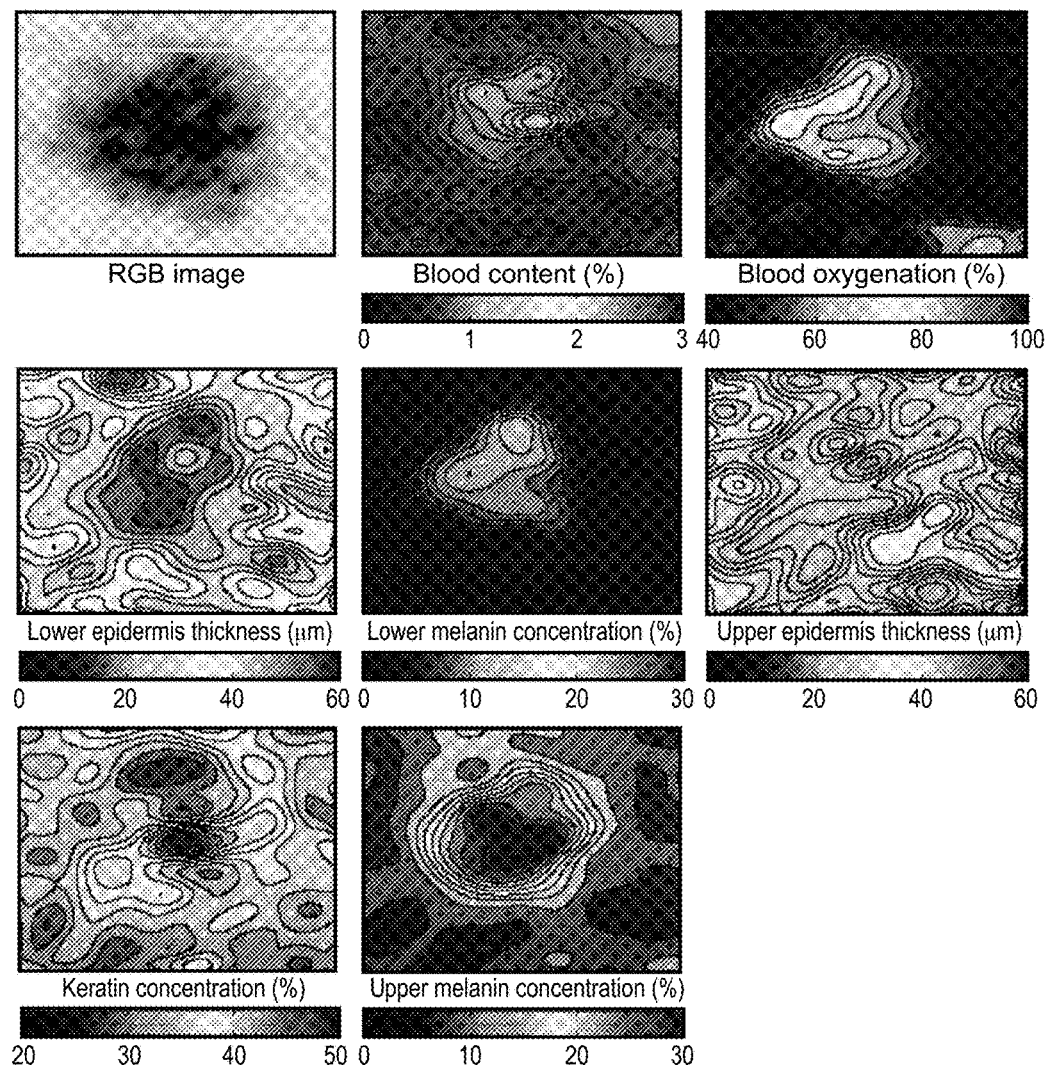
FIG. 7 shows exemplary spatial distribution maps of 7 parameters for a nevus.
Figure 8:
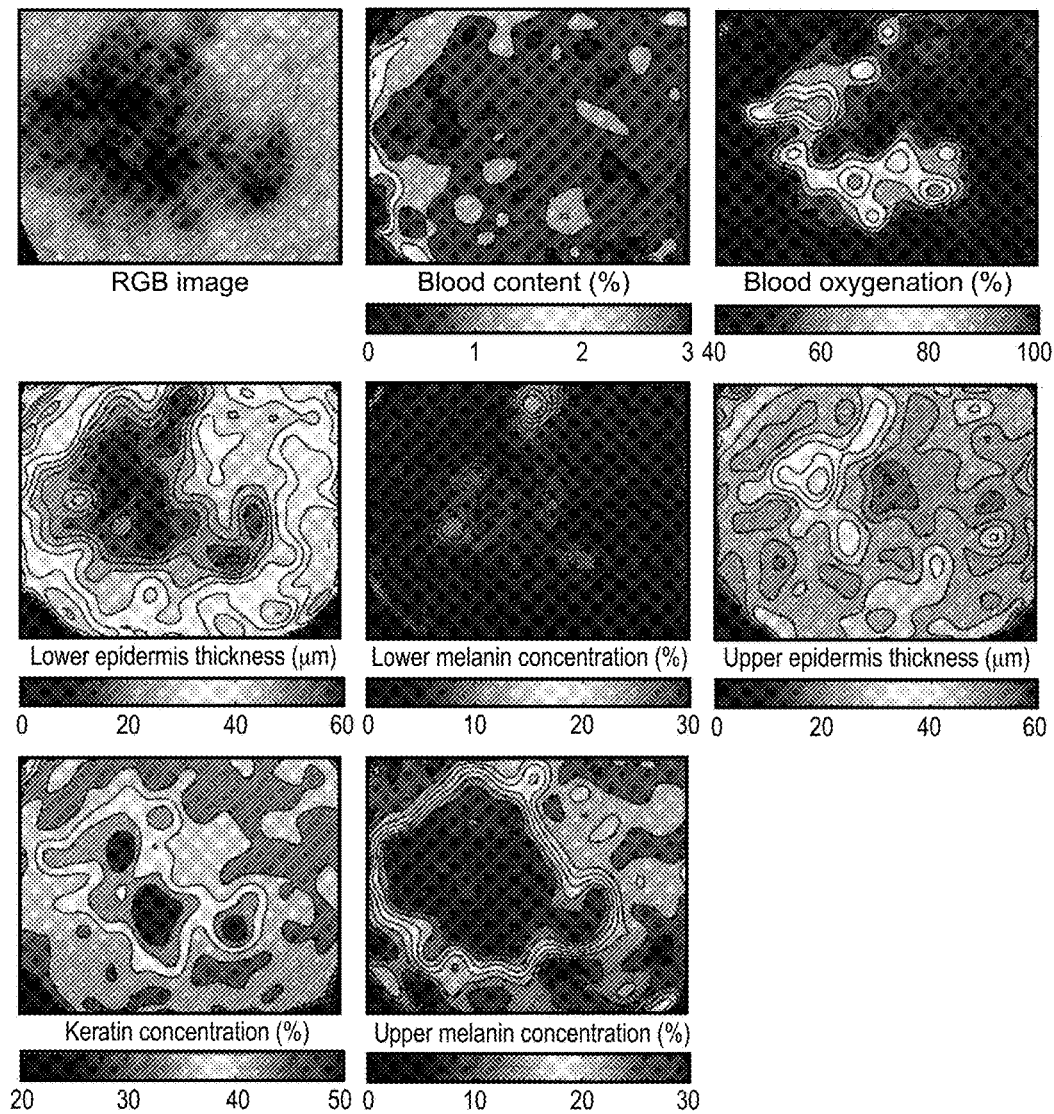
FIG. 8 shows exemplary spatial distribution maps of 7 parameters for a melanoma.

On the basis of established absorption and transmission spectra for known skin chromophores and mathematical modeling of skin reflectance, the images from each set are used to derive maps of the lesions showing spatial distribution for the following 7 parameters (i) percentage of hemoglobin; (ii) percentage of hemoglobin oxygenation; (iii) upper epidermal thickness; (iv) lower epidermal thickness; (v) percentage of upper melanosome concentration; (vi) percentage of lower melanosome concentration; and (vii) percentage of keratin concentration. FIGS. 7 and 8 show exemplary spatial distribution maps for these seven parameters. FIG. 7 shows a series of spatial distribution maps for a skin lesion determined to be a nevus while FIG. 8 shows a series of spatial distribution maps for a skin lesion determined to be a melanoma. The seven mapped parameters vary and are different for normal and malignant tissues.

From each map, an entropy value is calculated. Cross entropy values may then be calculated among various pairs of maps which may be derived from the ensemble of different images recorded for different wavelengths and angles of illumination and detection. For example, from the spatial distribution of the melanosome concentration, one can compute the entropy of the parameter as the sum of the melanosome concentration multiplied by its logarithm and integrated over the area of the lesion. The entropy value provides a measure of the disorder in any one of the maps, and the cross entropy provides a measure of the correlation between different maps.

In the development of a robust diagnostic procedure, it is important to keep in mind that the final diagnosis to the largest degree possible should be independent of the following:

The robustness of the measurement probe;

Clinical measurement errors due to: bad contact between the probe and skin, too high or too low pressure between the probe and the skin, or too much or too little gel or oil applied between the probe and the skin;

Azimuth angle between the probe and the lesion (for asymmetric lesions);

Incorrect exposure time (which may be fixed independent of skin type);

Location of lesion in the picture frame;

Skin type;

Lesion location on the patient's body; or

Changes in the physiological state of the patient due to, for example, but not limited to, jumps in the blood pressure or blood oxygenation;

Further, a final diagnosis should be insensitive to errors and assumptions made in the pre-processing of the data.

From a set of digital reflectance images of a lesion generated by the OTD device, the optical properties of a lesion can be determined by the methods of PCT WO 02/069792 A1, and maps of the spatial distribution of various parameters across a skin lesion and morphology parameter values, can be made in a number of ways, including by the method of U.S. Provisional Patent Application No. 61/037,503.

Figure 1:
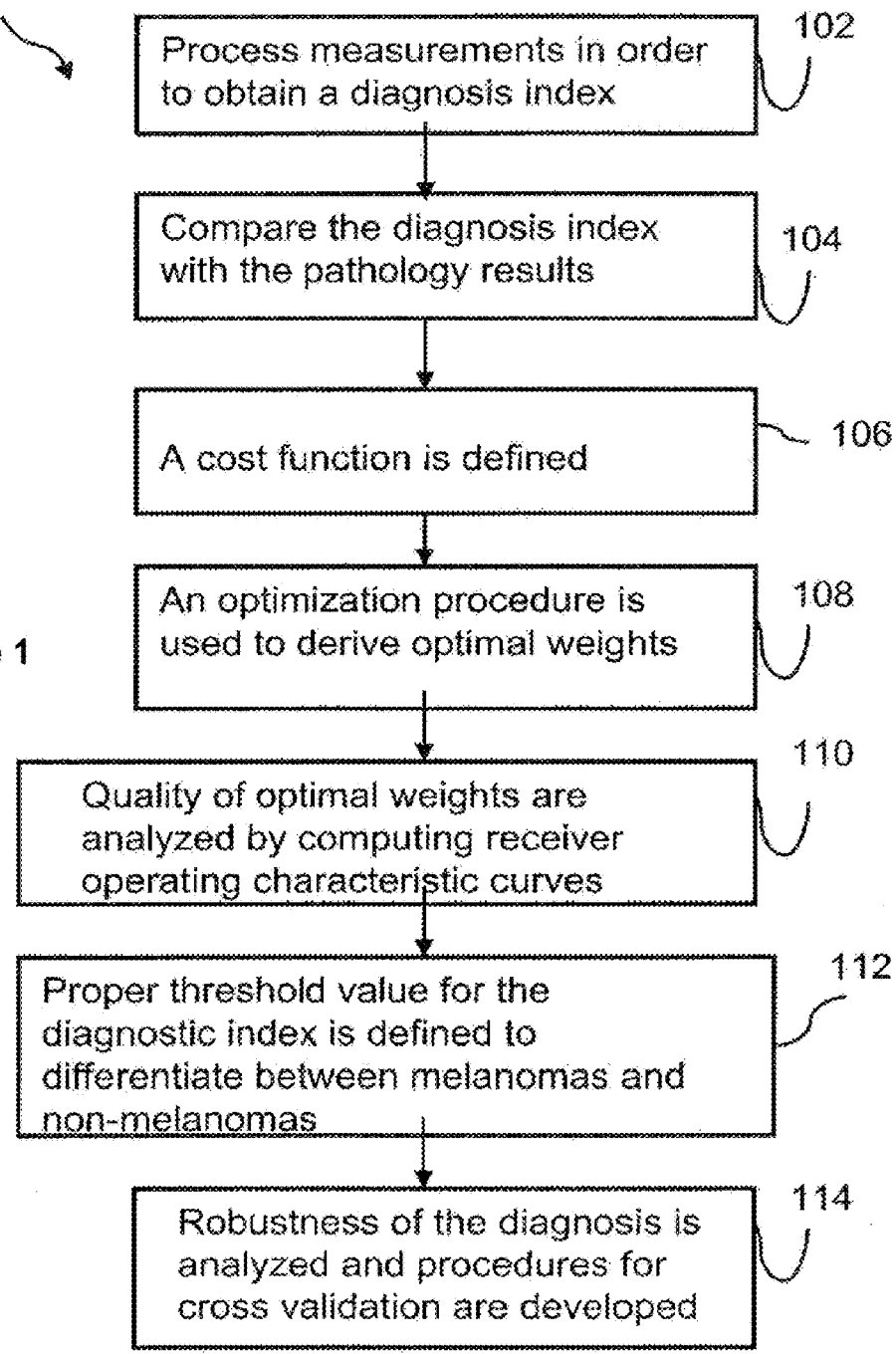
FIG. 1 is a flow chart illustrating a method in accordance with an embodiment of the present invention.
Figure 6:
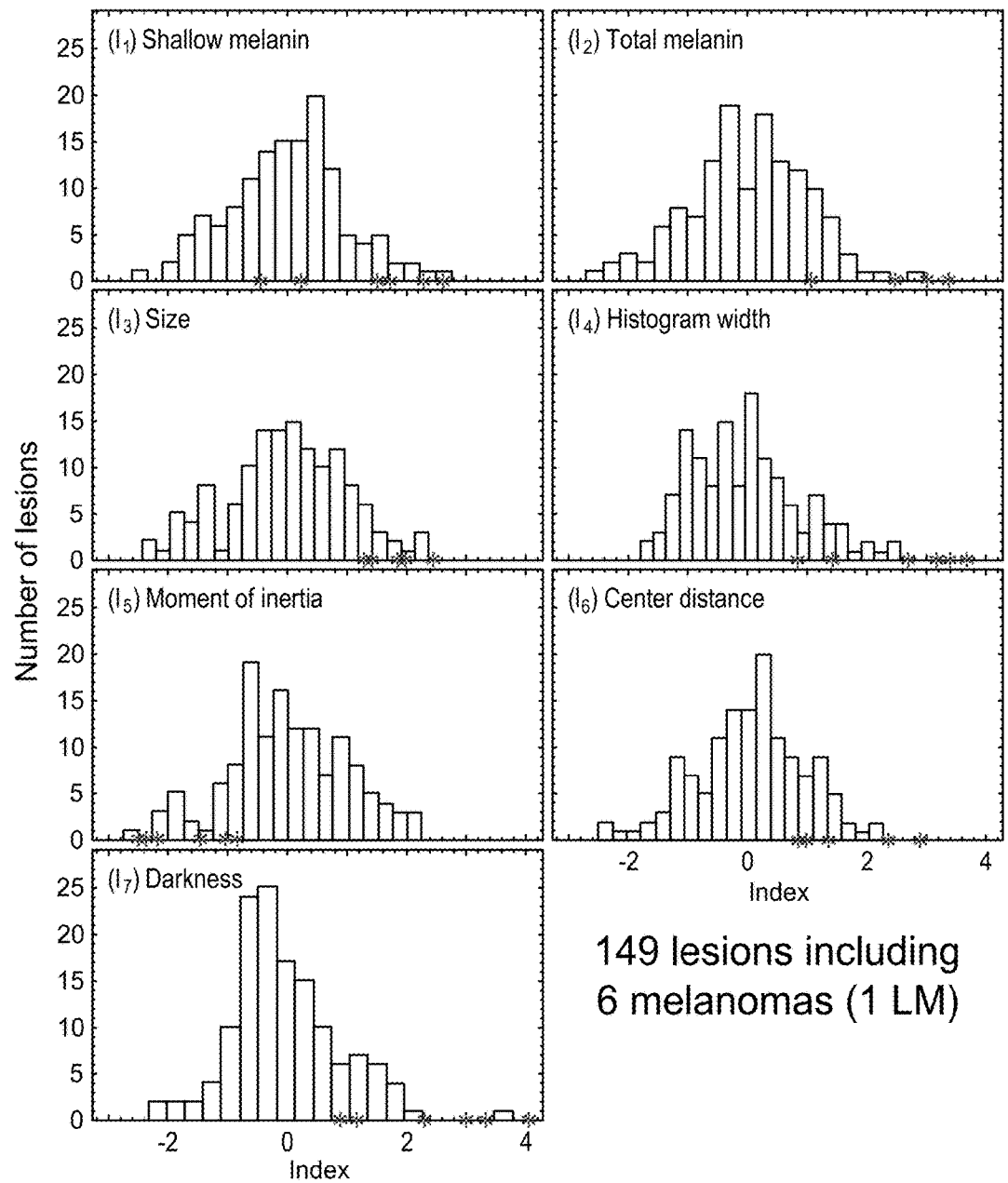
FIG. 6 shows distribution charts for 7 morphology parameters measured in 149 lesions.

In an embodiment of the present invention, a method 100, as shown in FIG. 1, includes considering a set of maps of the spatial distribution of one or more parameters such as, percentage of hemoglobin; percentage of hemoglobin oxygenation; upper epidermal thickness; lower epidermal thickness; percentage of upper melanosome concentration; percentage of lower melanosome concentration; and percentage of keratin concentration. A number of morphology parameters are also considered which may include, for example, area (size), relative moment of inertia, shallow melanin, total melanin, histogram width, center distance, and darkness. Distribution for seven of these morphology parameters among a sample of 149 lesions (including 6 melanomas) is shown in FIG. 6. A diagnosis may be made from the maps and morphology parameters using the following steps. At step 102, for each available measurement, process the measurements in order to obtain a diagnosis. This diagnosis is obtained by using a set of maps (at least one for each parameter) as well as a set of morphology parameters derived from reflectance images of the skin lesion generated by the OTD device. At step 104, compare the diagnosis obtained in step 102 with pathology results obtained from clinical data as follows: patients with suspicious lesions are referred for scanning by the OTD device; after scanning, lesions are biopsied for histopathologic examination by dermatopathologists, and a diagnosis is provided. At step 106, a cost function consisting of the following is defined: a master term (including pathology), constraints, regularization, and Occam's rule. The master term is specifically designed to discriminate between malignant and benign lesions. Constraints are used to take advantage of a priori information about the covariance of the measurements, while regularization is used to suppress variations in the measurements, which do not contribute to the correct diagnosis. Some of the data derived from the maps (e.g., entropy of the parameters described above and cross entropy between maps) as well as some of the morphology parameters may not contribute significantly to the diagnosis upon application of the cost function. Occam's rule is designed to exclude insignificant parameters to provide a streamlined diagnosis determination with the least amount of parameters required to still maintain accuracy, specificity, and sensitivity. At step 108, an optimization procedure is used to derive optimal weights. The optimization is an iterative process in which the weights are adjusted until the number of false positives (diagnosing the lesion as malignant when it actually is benign) becomes as small as possible when at the same time the number of false negatives is zero (no malignant lesions missed by the diagnosis). At step 110, the quality of the optimal weights is analyzed by computing receiver operating characteristic (ROC) curves. A ROC curve is a graphical display of the sensitivity vs. specificity, where the sensitivity is the probability of correctly diagnosing a malignant lesion, and the specificity is the probability of correctly identifying a benign lesion. At step 112, a threshold value for the diagnostic index, D, is defined to differentiate between melanomas and non-melanomas. A threshold value is chosen in accordance with the desire to discriminate between benign and malignant lesions in such a way that the diagnostic index for malignant lesions is well enough separated from those of benign lesions so that errors in the measurement procedure are properly taken into account. At step 114, the robustness of the diagnosis is analyzed and procedures for cross validation are developed. Given a set of data generated by the OTD device and a corresponding set of pathology results, the method may be used to find optimized weights for the entire data set and to determine a threshold value. But the method may also be used to find optimized weights for a subset of the entire data set obtained by excluding some of the measurements wherein, for example, parameters or measurements found to be insignificant are disregarded and removed from the determination. By creating several such subsets, the robustness of the method can be tested by assessing how well the method works on such subsets. This process is referred to as cross validation.

For the sake of clarity, details of the diagnostic procedure of the method 100 are further explained. In order to facilitate the solution of the global optimization problem involving our entire processing chain, which depends on a large number of processing parameters, measurements of the spatial distribution maps and the morphology parameters obtained using current processing codes should be considered. Further, the maps and morphology parameters will be noisy (irreproducible), reflecting both noisy initial digital images of the same lesion and noise arising from the current non-optimal processing.

The diagnostic procedure, when properly optimized, shall give a diagnosis that is insensitive to variations in the input parameters due to experimental factors, such as, but not limited to, camera-tissue interface pressure, lesion-camera angular orientation and positioning. Further, the factors may be dependent on data acquisition and processing. Through proper optimization, variations between different reflectance measurements of the same lesion and corresponding variations in the maps and morphology parameters may be automatically suppressed during processing. After optimization of the weights, all maps and morphology parameters will be processed in an optimal manner by application of the optimized weights in determining diagnoses.

Figure 2:
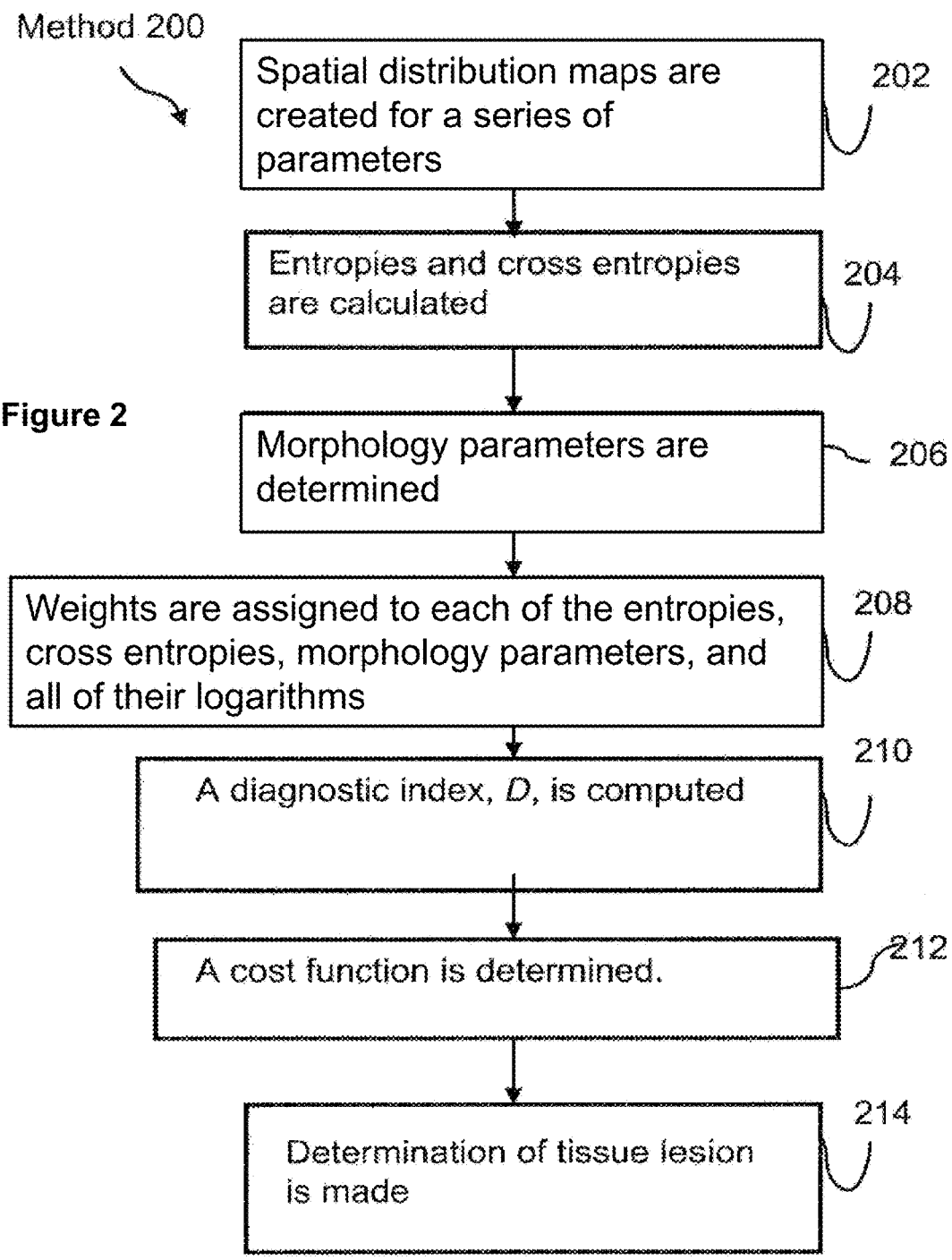
FIG. 2 is a flow chart illustrating another method in accordance with an embodiment of the present invention.

In order to obtain an optimum diagnosis, another method is shown in FIG. 2. The following steps, method 200, are taken for each lesion measurement. At step 202, maps are computed, including estimated uncertainties. At step 204, entropies and cross entropies are calculated for the probability density function associated with each of the maps. At step 206, morphology parameters are calculated from the compressed nadir images for the green and the Near Infrared (NIR) channel. At step 208, weights are assigned to each of the entropies and cross entropies and their logarithms and to each of the morphology parameters and their logarithms. For example, there may be 7 maps, and 10 morphology parameters. Therefore, there would be 28 values for the map derived entropies and cross entropies, 28 values for their logarithms and 10 values for the morphology parameters and 10 values for their logarithms. In this example, 76 weights, $w_i$, would be assigned. At step 210, a diagnostic index, D, is computed associated with the diagnosis of melanoma in the following manner: $D=w^T p$, where w is a column vector (the superscript T denotes transpose) consisting of 76 weights $w_i$ (to be optimized as explained below), p is a column vector of 76 elements or input values consisting of 28 entropies and cross entropies and their 28 logarithms together with 10 morphology parameter values and their 10 logarithms, and D is a value of the diagnostic index computed for every lesion being examined.

In step 212, a cost function is determined. The cost function, as discussed in method 100, may be defined by a general expression, such as the following:

$$J(w)=J_0(w)+\alpha_1 J_1(w)+\alpha_2 J_2(w)+\alpha_3 J_3(w),$$

where $\alpha_1$, $\alpha_2$ and $\alpha_3$ are coefficients to be determined, and $J_0(w)$ is called the master term of the cost function, $J_1(w)$ represents constraints of the cost function, $J_2(w)$ represents self-adaptive regularization of the cost function, and $J_3(w)$ is called Occam's rule.

For exemplary purposes, an example of how the diagnostic procedure may be implemented is shown using a special case of discrimination between benign pigmented lesions and malignant melanomas. The total set of obtained measurements under consideration is divided into two subsets. One subset consists of all non-melanomas, and the other subset consists of all melanomas, the total number of the latter being N. For any chosen weight vector w, the distribution of the diagnostic indices is calculated for the set of non-melanomas being considered. The average value of this distribution is $\mu(w)$, and the standard deviation squared is $\sigma^2(w)$. The master term of the cost function may be given by:

$$J_0(w) = -\frac{1}{N} \sum_{n=1}^{N} \frac{D_n^M(w) - \mu(w)}{\sigma(w)} \left[ 1 + \tanh\left(-\beta \cdot \frac{D_n^M(w) - \mu(w)}{\sigma(w)}\right) \right]$$

where $D_n^M(w)$ is the diagnostic index for melanoma number n as determined by pathology, and $\beta$ is a penalizing factor, which must be positive. Here, the difference $D_n^M(w) - \mu(w)$ should be positive and as large as possible in order to minimize the value of the master term $J_0(w)$. The master term of the cost function is designed to be quadratic around its minimum value so that it works well with standard optimization methods based on quadratic forms. It is also designed to penalize low $D_n^M(w)$ values. Thus, a master term of the cost function is created that pushes all differences $D_n^M(w) - \mu(w)$ for melanomas towards higher values, while pushing corresponding differences for non-melanomas towards lower values.

Multiplication of the weight vector by any positive constant will not change the distribution of the diagnostic indices. Thus, the length of w may be constrained by the second term in the following equation:

$$J(w) = J_0(w) + \alpha_1 (w^*w - w_0^*w_0)^2 + \alpha_2 J_2(w) + \alpha_3 J_3(w),$$

where $w_0$ is the initial guess for the weight vector. The second term in the equation above constrains the end points of the weight vectors w to lie on the surface of a hypersphere in 76 (per the earlier example) dimensions of radius $w_0$. If the end point of the weight vector w lies outside or inside the surface of the hypersphere, its length will be longer or shorter than the length of the vector $w_0$, which is the radius of hypersphere. The constraint term $\alpha_1(w^*w - w_0^*w_0)^2$ will be non-negative, and will increase the further away from the surface of the hypersphere the end point of the weight vector w lies. Thus, by adding the constraint term with positive value of the coefficient $\alpha_1$ to the cost function, which is to be minimized, the optimization routine is constrained to look for solutions w that have end points close to the surface of the hypersphere of radius $|w_0|$.

Probabilistic (soft) constraints on the weight vector w will be required to get a well-posed optimization problem. Such constraints should include a priori information about the covariance. A self-adaptive regularization, which exploits the use of a specific function associated with Fisher's information operator may be used. This kind of regularization allows for automatic suppression of variations in those elements of w, which do not contribute to the correct diagnosis.

It is possible that some of the 28 map derived values and the 10 morphology values may not be vital for the diagnosis. In order to exclude insignificant parameters, the fourth term $J_3(w)$ in the cost function equation is included. Thus, the fourth term of the cost function in terms of Shannon's entropy is:

$$J_3(w) = -s(w) \cdot \ln s(w)$$

where $s(w)$ is the probability density vector function of the weight vector w, with components given by:

$$s_i = |w_i| \bigg/ \sum_{i=1}^{76} |w_i|;$$

$$\sum_{i=1}^{76} s_i = 1$$

and where $\ln s(w)$ is a vector with components ($\ln s_1$, $\ln s_2$, ..., $\ln s_{76}$).

Note that $J_3(w)$ is non-negative, and that its smallest value of zero occurs if all weights are zero, except for one of them. Since the goal is to minimize the cost function, the Shannon entropy should be as small as possible, i.e. as many weights as possible should be zero, so that the corresponding physiology/morphology or morphology parameters from the input parameter vector p can be excluded. For this reason the term involving $J_3(w)$ is called Occam's rule.

Occam's rule may not be sufficient in order to exclude insignificant parameters. Therefore, the 76-element weight vector may be a sum of the initial weight vector $w_0$ and a superposition of certain basis vectors $v_j$ with coefficients $a_j$:

$$w = w_0 + V a$$

where V is a 76×L matrix, composed of L<76 basis vectors (column vectors: $v_1, v_2, v_3, \ldots, v_L$), each having 76 components, and a is a column vector with L components $a_j$ ($j=1, 2, \ldots, L$). Further, the number L is determined through the use of an information operator. Also, the basis vectors $v_1, v_2, v_3, \ldots, V_L$, and the coefficients $a_j$ of interest may be determined. An information operator $H^*_0$ is defined as follows:

$$H^*_0 = H_0 C_U^{-1} C_P C_U^{-1} H_0,$$

where $H_0$ is the Hessian matrix associated with the master term of the cost function, i.e.

$$H_0(w) = \left[ \frac{\partial^2}{\partial w^2} J_0(w) \right]_{w_0}.$$

Here $w_0$ is the initial value of w. $C_p$ is the covariance matrix of the input parameter vectors p for all measurements:

$$C_p = \langle (p - \langle p \rangle)(p - \langle p \rangle)^T \rangle$$

and $C_U$ is the covariance matrix of the measurement errors:

$$C_U = C^*_U + kI$$

where I is the unity matrix, k is a regularization factor to ensure the invertibility of $C_U$, and $C^*_U$ is given by $$C^*_U = \langle \langle (p_{lesion} - \langle p_{lesion} \rangle)(p_{lesion} - \langle p_{lesion} \rangle)^T \rangle \rangle = \langle (C_p)_{lesion} \rangle$$

where $(C_p)_{lesion}$ is the covariance matrix for all measurements performed on one lesion, and where the final averaging is over all lesions.

Note that the information operator contains all pathological information as well as information about measurement uncertainties and the ranges of variation of the input parameters.

The expression for the information operator can be interpreted as follows. The larger the value of $H^*_0$, the smaller the measurement errors (represented by $C_U$), the wider the range of the input parameters (represented by $C_p$), the more information we can obtain for diagnostic purposes.

Next, the eigenvalue problem for the information operator)

$$H^*_0 v^{(0)} = \lambda^{(0)} v^{(0)}$$

where $v^{(0)}$ is an eigenvector that depends on the initial weight vector $w_0$, and $\lambda^{(0)}$ is the eigenvalue. However, the tangential projection e of the eigenvector is $$e = (I - w_0 w_0^T) v^{(0)}$$

where $w_0$ is the initial weight vector. The vectors e, which are not orthonormal, but which satisfy the constraint that the end point of the weight vector should lie on the hypersphere, will be used as basis vectors to represent w.

Next, the set of eigenvectors is ordered according to the magnitude of the product of the eigenvalue $\lambda_i$ the length squared of the tangential projection $e_i = (l_i = |\lambda_i| |e_i|^2)$, and then only those tangential projections $e_i$ of the eigenvector are considered that satisfy the inequality $$l_i = |\lambda_i||e_i|^2 > \alpha\{(|\lambda||e|^2\}_{max}$$

where $\alpha$ is a threshold value to be determined that is positive and less than a certain pre-selected value, currently set to 0.01. The larger the value of $l_i$, the larger the information content associated with the corresponding basis vector $e_i$.

Now the weight vector is defined by replacing V by E in the previous expression for w:

$$w = w_0 + E\ a$$

where E is a 76×L matrix, composed of L basis vectors (column vectors: $e_1$, $e_2$, $e_3$, . . . $e_L$), each having 76 components, and a is a column vector with L components, the number L being the maximum value of i. The vector a will be determined by the optimization.

Using the representation above for w, we redefine the cost function as follows:

$$J^*(a) = J^*_0(a) + \alpha_1 J^*_1(a) + \alpha_2[a \cdot (R\ a)] + \alpha_3 J^*_3(a)$$

where $$J^*(a) = J(w) = J(w_0 + E\ a);\ J_n^*(a) = J_n(w) = J_n(w_0 + E\ a);$$
$$(n = 0, 1, 2, 3).$$

The regularization term $a \cdot (R\ a)$ contains the diagonal matrix R with elements $(l_1^{-1}, l_2^{-1}, \ldots, l_L^{-1})$, where $l_i = |\lambda_i| |e_i|^2$, and L is the maximum value of i.

The regularization term is constructed such that the smaller the information content in a certain direction, the shorter the step taken in that direction.

One or more steps of the methods of the invention may be carried out by a computer 105 including image generation, spatial distribution map creation, determination of entropy and cross entropy values and production of a diagnostic index value. A computer 105 may also be used to define a cost function comprising the determined values for plurality of investigated lesions with known pathology information and to solve an optimization problem to determine optimized weight values.

Example 1

In order to investigate the accuracy and robustness of the methods of the invention, they were applied to a clinical data set from 125 pigmented lesions. Three OTD measurements (each consisting of 30 images) were taken of each lesion, making the total number of measurements 125×3=375. Some of the measurements were discarded because of measurement errors, reducing the total number of useful measurements to 342.

A receiver operating characteristic (ROC) curve (as defined here) is a graphical plot of sensitivity vs. specificity. By applying the method of the present invention to the clinical data set described above, the sensitivity was found to be 1 (i.e. 100%) for any specificity below 0.914 (i.e. 91.4%). The area underneath the ROC curve should be equal to 1 in order to have a sensitivity of 100% for a specificity of 100%. The application to clinical data just mentioned showed that a reduction of the value of the master term of the cost function is highly correlated to an increase in the area underneath the ROC curve.

The optimization may be performed in accordance with the described procedure. The optimization is an iterative process, where the optimized weight vector from a given iteration is used as the input weight vector to the next iteration. For example, a total of 8 iterations may be used for each optimization, and the weights for each of the iterations may be stored. The optimization may be performed on any subset. In this example, the criterion used for accepting a weight vector was that it should give a specificity value larger than 90% at 100% sensitivity for all subsets.

The described method may be used to find optimized weights for a few different subsets of the entire data set. The subsets were created by starting from the entire set of all clinical measurements (342) and excluding some of the measurements. One subset was created by dividing the total set into three equal parts, each consisting of every third measurement, and then excluding one third of the total subset, so that the remaining subset contained two thirds of the entire data set. In the current data set there are a total of eleven melanomas. Nine different subsets were created by excluding all measurements that had been performed on one of the eleven lesions being a melanoma according to the pathology report.

Covariance matrices are used in the information operator and Occam's rule is used in the cost function, in order to suppress insignificant weights (and corresponding input parameters). In the clinical data described above, several weights were found to be very small and were set equal to zero. The new weight vector with fewer non-zero weights was tested for acceptance. With a correct selection of insignificant weights, the specificity at 100% sensitivity for all subsets did not change noticeably. With the present invention, weights optimized using several different subsets were found to be acceptable with as many as 26 of the 76 weights set equal to zero. See Swanson, et al., 2010, Optical Transfer Diagnosis of Pigmented Lesions, Dermatol Surg 36:1979-1986; Swanson, et al., 2009, Optical transfer diagnosis of pigmented lesions: a pilot study, Skin Res Tech, 15, 330-337; the contents of each of which are incorporated herein by reference in their entirety.

No element, act, or instruction used in the present disclosure should be construed as critical or essential unless explicitly described as such. In addition, as used herein, the article "a" is intended to include one or more items. Where only one item is intended, the term "one" or similar language is used.

It will be understood that various modifications may be made to the embodiments disclosed herein. Therefore, the above description should not be construed as limiting, but merely as exemplifications of the various embodiments of the present disclosure. Those skilled in the art will envision other modifications within the scope and spirit of the claims appended hereto.

What is claimed is:

1. A method for discriminating between benign and malignant skin lesions, the method comprising the steps of:
generating a plurality of spectral reflectance images of a skin lesion at a plurality of angles of illumination and detection using an optical transfer diagnosis (OTD) device without repositioning the OTD device, wherein the OTD device comprises a spectral reflectance meter consisting of a measurement head with a plurality of fixed light-emitting diode (LED) lamps and a plurality of cameras wherein the plurality of LED lamps are configured within the OTD device to provide polar angles between 30 and 45 degrees relative to a central opening in the measurement head and relative azimuth angles between 34 and 145 degrees relative to the central opening in the measurement head and wherein the plurality of cameras are configured within the OTD device to provide polar angles between 0 and 45 degrees relative to the central opening in the measurement head, and relative azimuth angles between 0 and 180 degrees relative to the central opening in the measurement head, wherein the central opening in the measurement head is placed above the skin lesion while the plurality of spectral reflectance images is generated;
creating, for each of a plurality of parameters, a spatial distribution map of the skin lesion from the plurality of spectral reflectance images;
determining entropy values for each of the spatial distribution maps;
determining cross entropy values between pairs of the spatial distribution maps;
determining, from the plurality of spectral reflectance images, a plurality of morphology parameter values;
calculating, for each of the determined values, a logarithm of that determined value;
for each of a plurality of weight values, applying that weight value to a corresponding one of the determined values and calculated values to thereby produce a diagnostic index value;
comparing the diagnostic index value to a threshold value to thereby indicate if the skin lesion is a malignant skin lesion.

2. The method of claim 1, further comprising defining a cost function comprising the determined values for plurality of investigated lesions with known pathology information and solving an optimization problem to determine the plurality of weight values.

3. The method of claim 2, wherein the cost function includes a master term with pathology information from the plurality of investigated lesions.

4. The method of claim 1, wherein the generating step further comprises recording, with the OTD device, 30 spectral reflectance images at 10 different wavelengths between 365-1000 nm.

5. The method of claim 1, wherein the plurality of parameters of the spatial distribution maps comprises percentage of hemoglobin, percentage of hemoglobin oxygenation, upper epidermal thickness, lower epidermal thickness, percentage of upper melanosome concentration, percentage of lower melanosome concentration, or percentage of keratin concentration.

6. The method of claim 1, wherein the plurality of parameters of the spatial distribution maps comprises percentage of hemoglobin, percentage of hemoglobin oxygenation, upper epidermal thickness, lower epidermal thickness, percentage of upper melanosome concentration, percentage of lower melanosome concentration, and percentage of keratin concentration.

7. A system for discriminating between benign and malignant skin lesions, the system comprising:
an optical transfer diagnosis (OTD) device comprising:
a measurement head with a plurality of fixed light-emitting diode (LED) lamps and a plurality of cameras wherein the plurality of LED lamps are configured within the OTD device to provide a plurality of polar angles between 30 and 45 degrees relative to a central opening and relative azimuth angles between 34 and 145 degrees relative to the central opening and wherein the plurality of cameras are configured within the OTD device to provide a plurality of polar angles between 0 and 45 degrees relative to the central opening, and relative azimuth angles between 0 and 180 degrees relative to the central opening;
a control unit in electronic communication with the measurement head; and
a support arm coupled to the measurement head;
a computer in electronic communication with the OTD device and operable to:
receive a plurality of spectral reflectance images of a skin lesion from the optical transfer diagnosis (OTD) device;
create, for each of a plurality of parameters, a spatial distribution map of the skin lesion from the plurality of spectral reflectance images;
determine entropy values for each of the spatial distribution maps;
determine cross entropy values between pairs of the spatial distribution maps;
determine, from the plurality of spectral reflectance images, a plurality of morphology parameter values; and
calculate, for each of the determined values, a logarithm of that determined value;
for each of a plurality of weight values, apply that weight value to a corresponding one of the determined values and calculated values to thereby produce a diagnostic index value.

8. The system of claim 7, configured to capture 30 spectral reflectance images of a skin lesion at 10 different wavelengths between 365-1000 nm.

9. The system of claim 7, wherein the computer is further operable to compare the diagnostic index value to a threshold value to thereby indicate if the skin lesion is a malignant skin lesion.

10. The system of claim 7, wherein the computer is further operable to define a cost function comprising the determined values for plurality of investigated lesions with known pathology information and solving an optimization problem to determine the plurality of weight values.

11. The system of claim 7, wherein the plurality of parameters of the spatial distribution maps comprises percentage of hemoglobin, percentage of hemoglobin oxygenation, upper epidermal thickness, lower epidermal thickness, percentage of upper melanosome concentration, percentage of lower melanosome concentration, or percentage of keratin concentration.

12. The system of claim 7, wherein the plurality of parameters of the spatial distribution maps comprises percentage of hemoglobin, percentage of hemoglobin oxygenation, upper epidermal thickness, lower epidermal thickness, percentage of upper melanosome concentration, percentage of lower melanosome concentration, and percentage of keratin concentration.

13. The system of claim 7, wherein the cost function includes a master term with pathology information from the plurality of investigated lesions.

* * * * *